United States Patent [19]

Meyer

[11] 4,014,870

[45] Mar. 29, 1977

[54] STILBENE COMPOUNDS

[75] Inventor: Hans Rudolf Meyer, Binningen, Switzerland

[73] Assignee: Ciba-Geigy Corporation, Ardsley, N.Y.

[22] Filed: June 10, 1975

[21] Appl. No.: 585,539

[30] Foreign Application Priority Data

June 12, 1974 Switzerland .................. 8031/74
June 12, 1974 Switzerland .................. 8035/74

[52] U.S. Cl. .................. 260/240 CA; 162/162; 252/301.24; 260/240 D; 260/307 D
[51] Int. Cl.$^2$ .................. C07D 263/54
[58] Field of Search .................. 260/240 CA, 240 D

[56] References Cited

UNITED STATES PATENTS

| | | | |
|---|---|---|---|
| 3,133,916 | 5/1964 | Duennenberger | 260/240 CA |
| 3,577,411 | 5/1971 | Liechti et al. | 260/240 CA |
| 3,586,673 | 6/1971 | Bloom | 260/240 CA |
| 3,627,758 | 12/1971 | Weber et al. | 260/240 D |
| 3,682,900 | 8/1972 | Liechti et al. | 260/240 CA |
| 3,872,114 | 3/1975 | Saam et al. | 260/240 D |
| 3,901,883 | 8/1975 | Liechti et al. | 260/240 D |

OTHER PUBLICATIONS

Bloom, Def. Pub., 857 O.G. 696.
Bloom, Def. Pub., 861 O.G. 369.

*Primary Examiner*—Arthur P. Demers
*Attorney, Agent, or Firm*—Joseph G. Kolodny; Edward McC. Roberts; Prabodh I. Almaula

[57] ABSTRACT

New stilbene compounds, a process for their preparation as well as a process for optically brightening organic materials on using said stilbene compounds are disclosed.

8 Claims, No Drawings

STILBENE COMPOUNDS

The present invention relates to new stilbene compounds, a process for their manufacture and their use as optical brighteners for high-molecular organic materials.

These new stilbene compounds correspond to the formula

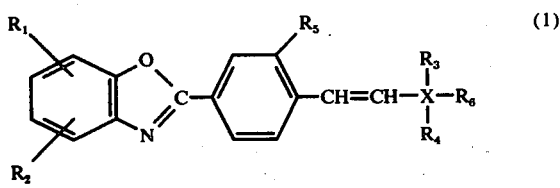

wherein X denotes a phenyl, naphthyl or 4-biphenyl radical, $R_1$ denotes hydrogen, alkyl having 1 to 4 carbon atoms, alkoxy having 1 to 4 carbon atoms, chlorine, cyclohexyl, benzyl, α,α-dimethylbenzyl, alkylsulphonyl having 1 to 4 carbon atoms, phenylsulphonyl, carbalkoxy having 2 to 5 carbon atoms, carboxyl, carbamoyl, sulpho or sulphamoyl or, conjointly with $R_2$, in the 5,6-position, denotes the trimethylene radical and, if X denotes phenyl, conjointly with $R_2$, in the 4,5-position, also denotes the 1,3-butadienylene radical, $R_2$ denotes hydrogen, alkyl having 1 to 4 carbon atoms, alkoxy having 1 to 4 carbon atoms, or chlorine or, conjointly with $R_1$, in the 5,6-position, denotes the trimethylene radical and, if X denotes phenyl, conjointly with $R_1$, in the 4,5-position, also denotes the 1,3-butadienylene radical, $R_3$ denotes hydrogen or sulpho or, if X denotes phenyl, also alkyl having 1 to 4 carbon atoms, alkoxy having 1 to 4 carbon atoms, chlorine, carboxyl, carbalkoxy having 2 to 5 carbon atoms, cyano or, conjointly with $R_4$, denotes the methylenedioxy, trimethylene or tetramethylene radical, $R_4$ denotes hydrogen or, if X denotes phenyl, also alkyl having 1 to 4 carbon atoms, alkoxy having 1 to 4 carbon atoms, or chlorine or, conjointly with $R_3$, denotes the methylenedioxy, trimethylene or tetramethylene radical, $R_5$ denotes hydrogen, chlorine or sulpho, and $R_6$ denotes hydrogen or sulpho, the molecule containing at least one but not more than two sulpho groups.

Preferred carbamoyl and sulphamoyl radicals can be represented by the formulae

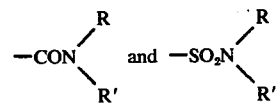

respectively, wherein R and R' independently of one another denote hydrogen or alkyl having 1 to 4 carbon atoms, or, conjointly with the nitrogen, denote the completion of a 5-membered to 7-membered non-aromatic ring, for example morpholino or piperidino.

"Carboxyl" and "sulpho" are to be understood respectively as the radicals —COOM and —SO₃M wherein M represents hydrogen or a salt-forming cation. Suitable salt-forming cations M are, in general, those of alkaline earth metals, for example of calcium, barium or magnesium, and, particularly, of alkali metals, for example of sodium or potassium, but also ammonium, optionally substituted by akyl or hydroxyalkyl having 1 to 4 carbon atoms. Besides hydrogen, the potassium cation and the sodium cation, in particular, are preferred in the meaning of M.

The 1,3-butadienylene radical corresponds to the completion of a fused benzene ring.

Within the scope of the invention, interest attaches above all to stilbene compounds of the formula

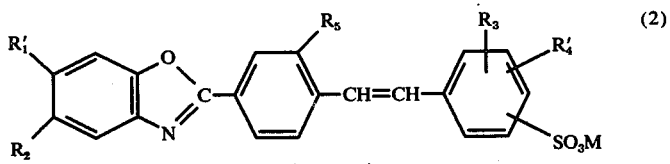

wherein $R_1'$ denotes hydrogen, alkyl having 1 to 4 carbon atoms, or alkoxy having 1 to 4 carbon atoms, or, conjointly with $R_2$, in the 5,6-position, denotes the trimethylene radical and, in the 4,5-position, denotes the 1,3-butadienylene radical, $R_2$ denotes hydrogen, alkyl having 1 to 4 carbon atoms, alkoxy having 1 to 4 carbon atoms, or chlorine or, conjointly with $R_1'$, in the 5,6-position, denotes the trimetylene radical and, in the 4,5-position, denotes the 1,3-butadienylene radical, $R_3$ denotes hydrogen, alkyl having 1 to 4 carbon atoms, alkoxy having 1 to 4 carbon atoms, chlorine, carboxyl, carbalkoxy having 2 to 5 carbon atoms, cyano or sulpho or, conjointly with $R_4'$, denotes the trimethylene or tetramethylene radical, $R_4'$ denotes hydrogen, alkyl having 1 to 4 carbon atoms, alkoxy having 1 to 4 carbon atoms, chlorine or, conjointly with $R_3$, denotes the trimethylene or tetramethylene radical, M denotes a hydrogen ion, alkali metal ion, alkaline earth metal ion, ammonia ion or amine salt ion, and $R_5$ has the meaning indicated above and the molecule contains at least one but not more than two sulpho groups, and stilbene compounds of the formula

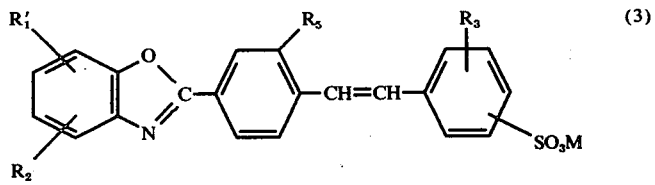

wherein $R_1'$, $R_2$, $R_3$, $R_5$ and M have the meaning indicated above.

Compounds which deserve particular mention are the stilbene compounds of the formula

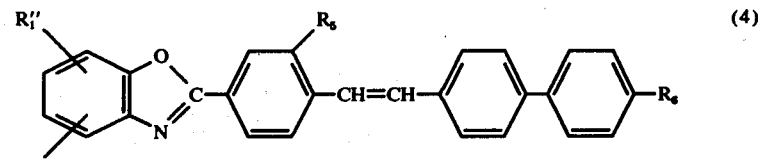
(4)

wherein $R_1''$ denotes hydrogen, alkyl having 1 to 4 carbon atoms, chlorine, cyclohexyl, benzyl, α,α-dimethylbenzyl, alkylsulphonyl having 1 to 4 carbon atoms, phenylsulphonyl, carbalkoxy having 2 to 5 carbon atoms, carboxyl, carbamoyl, sulpho or sulphamoyl or, conjointly with $R_2''$, in the 5,6-position, denotes the trimethylene radical, $R_2''$ denotes hydrogen, alkyl having 1 to 4 carbon atoms, or chlorine or, conjointly with $R_1''$, in the 5,6-position, denotes the trimethylene radical, $R_5$ denotes hydrogen, chlorine or sulpho and $R_6$ denotes hydrogen or sulpho, and the molecule contains at least one but not more than two sulpho groups, the stilbene compounds of the formula

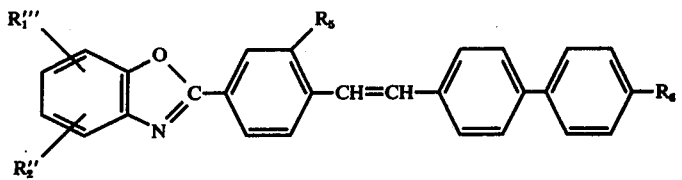
(5)

wherein $R_1'''$ denotes hydrogen, alkyl having 1 to 4 carbon atoms, chlorine, cyclohexyl, benzyl, α,α-dimethylbenzyl, alkylsulphonyl having 1 to 4 carbon atoms, carbalkoxy having 2 to 5 carbon atoms, carboxyl, sulpho or sulphamoyl or, conjointly with $R_2'''$, in the 5,6-position, denotes the trimethylene radical and $R_2'''$ denotes hydrogen, alkyl having 1 to 4 carbon atoms, chlorine or, conjointly with $R_1'''$, in the 5,6-position, denotes the trimethylene radical and $R_5$ and $R_6$ have the meaning indicated above, the stilbene compounds of the formula

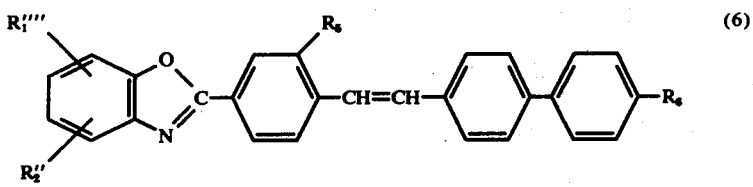
(6)

wherein $R_1''''$ denotes hydrogen, alkyl having 1 to 4 carbon atoms, chlorine, cyclohexyl, α,α-dimethylbenzyl, sulpho or carbalkoxy having 2 to 5 carbon atoms, or, conjointly with $R_2'''$, in the 5,6-position, denotes the trimethylene radical and $R_2''$ denotes hydrogen, alkyl having 1 to 4 carbon atoms or chlorine or, conjointly with $R_1''''$, in the 5,6-position, denotes the trimetylene radical and $R_5$ and $R_6$ have the meaning indicated above, and the stilbene compounds of the formula

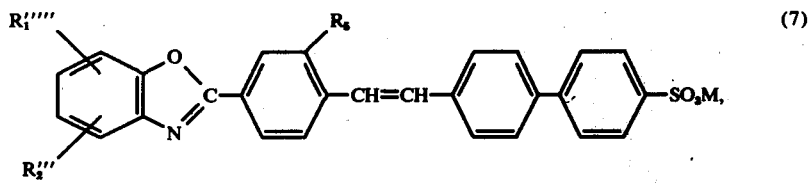
(7)

wherein $R_1'''''$ denotes hydrogen, alkyl having 1 to 4 carbon atoms, chlorine or carbalkoxy having 2 to 5 carbon atoms, $R_2'''$ denotes hydrogen, methyl or chlorine, and M denotes a hydrogen ion, alkali metal ion, alkaline earth metal ion, ammonium ion or amine salt ion and $R_5$ has the meaning indicated above.

Particular interest attaches to the compounds of the formula

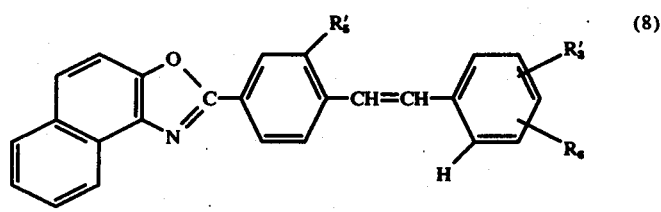
(8)

wherein $R_3'$ denotes hydrogen, alkyl having 1 to 4 carbon atoms, sulpho or chlorine, $R_5'$ denotes hydrogen or sulpho, and $R_6$ denotes hydrogen or sulpho and the molecule contains at least one but not more than two sulpho groups.

The present invention also relates to a process for the manufacture of the new compounds of the formulae (1) to (8), which is characterised in that, in order to manufacture, a) compounds of the formula (1), about 1 molar equivalent of a compound of the formula

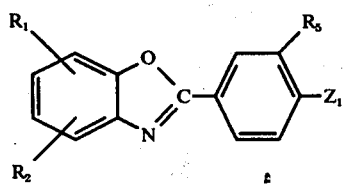
(9)

is reacted, if appropriate in the presence of a strongly basic alkali metal compound and in the presence of a, preferably hydrophilic, strongly polar solvent, with about 1 molar equivalent of a compound of the formula

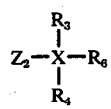
(10)

wherein $R_1$ to $R_6$ have the meaning indicated above and one of the symbols $Z_1$ and $Z_2$ denotes an O=CH group and the other denotes one of the groupings of the formulae

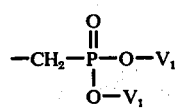
(11a)

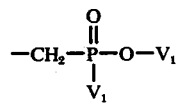
(11b)

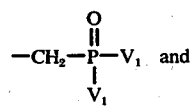
(11c)

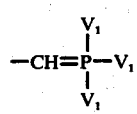
(11d)

wherein $V_1$ represents an alkyl radical which is optionally further substituted, preferably an alkyl radical having up to 6 carbon atoms, an aryl radical, preferably a phenyl radical, a cycloalkyl radical, preferably a cyclohexyl radical, or an aralkyl radical, preferably a benzyl radical, b. stilbene compounds of the formula (2) and (3), about 1 molar equivalent of a compound of the formula

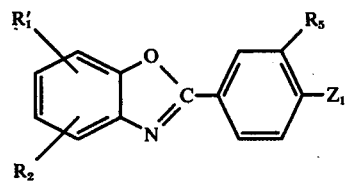
(12)

is reacted, if appropriate in the presence of a strongly basic alkali metal compound and in the presence of a, preferably hydrophilic, strongly polar solvent, with about 1 molar equivalent of a compound of the formula

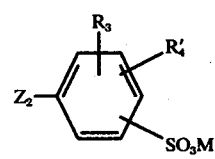
(13)

or

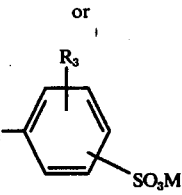
(14)

c. stilbene compounds of the formulae (4) to (5), about 1 molar equivalent of a compound of the formula

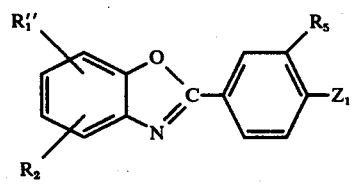
(15)

or

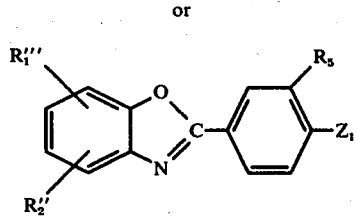
(16)

or

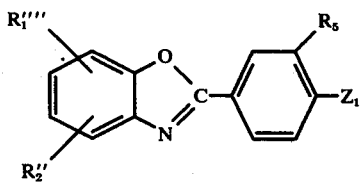
(17)

is reacted, if appropriate in the presence of a strongly basic alkali metal compound and in the presence of a, preferably hydrophilic, strongly polar solvent, with about 1 molar equivalent of a compound of the formula

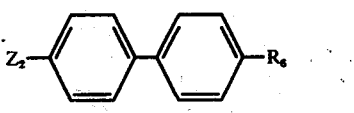

d. stilbene compounds of the formula (7), about 1 molar equivalent of a compound of the formula

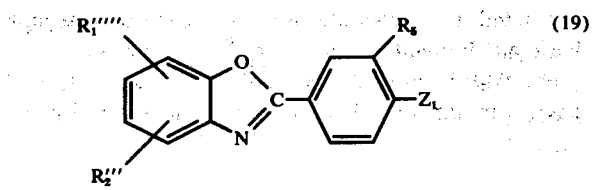

is reacted, if appropriate in the presence of a strongly basic alkali metal compound and in the presence of a, preferably hydrophilic, strongly polar solvent, with about 1 molar equivalent of a compound of the formula

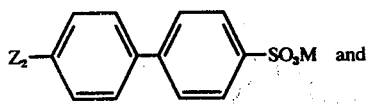

e. stilbene compounds of the formula (8), about 1 molar equivalent of a compound of the formula

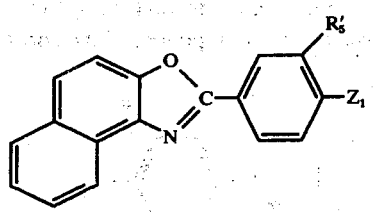

is reacted, if appropriate in the presence of a strongly basic alkali metal compound and in the presence of a, preferably hydrophilic, strongly polar solvent, with about 1 molar equivalent of a compound of the formula

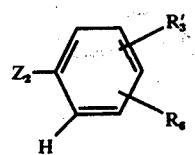

In the formulae (9) to (22), the various symbols have the meaning indicated respectively under the formulae (1) to (8).

In the preferred embodiment of the manufacturing process previously mentioned, $Z_1$ represents a radical of the formulae (11a) to (11d), particularly (11a), and $Z_2$ accordingly represents the O=CH group.

The compounds of the formulae (9) to (22) which are required as starting materials can be manufactured in analogy to processes which are in themselves known.

The manufacturing process is advantageously carried out in inert solvents. Examples of these which may be mentioned are hydrocarbons, such as toluene and xylene, or alcohols, such as methanol, ethanol, isopropanol, butanol, glycols, glycol ethers, such as 2-methoxyethanol, hexanols, cyclohexanol and cyclooctanol, and also ethers, such as diisopropyl ether, tetrahydrofurane and dioxane, as well as dimethylsulphoxide, formamide and N-methylpyrrolidone. Polar organic solvents, such as dimethylformamide and dimethylsulphoxide, are particularly suitable. Some of the reactions can also be carried out in aqueous solution.

The temperature at which the reaction is carried out, can vary within wide limits. It is determined α) by the stability of the solvent used towards the reactants, particularly towards the strongly basic alkali metal compounds, β) by the reactivity of the condensation reactants and γ) by the activity of the combination solvent-base as a condensation agent.

In practice, temperatures between about 10° and 100° C are therefore generally possible, particularly if dimethylformamide or dimethylsulphoxide is used as the solvent. The preferred temperature range is 20° to 60° C. However, under certain circumstances, higher temperatures can also be used, if this is desired for reasons of saving time or if a less active but, in return, cheaper condensation agent is to be employed: in principle, therefor, reaction temperatures in the range from 10° to 180° C are also possible.

Possible strongly basic alkali metal compounds are, above all, the hydroxides, amides and alcoholates (preferably those of primary alcohols containing 1 to 4 carbon atoms) of the alkali metals, and, for economic reasons, those of lithium, sodium and potassium are of predominant interest. However, in principle and in particular cases, alkali metal sulphides and carbonates, aryl alkali metal compounds, such as, for example, phenyl-lithium, or strongly basic amines (including ammonium bases, for example trialkylammonium hydroxides) can also be used with success.

The new compounds defined above exhibit a more or less pronounced fluorescence in the dissolved or finely dispersed state. They can be used for optically brightening the most diverse synthetic, semi-synthetic or natural organic materials or substances which contain such organic materials.

The following groups of organic materials, where optical brightening thereof is relevant, may be mentioned as examples of the above, without the survey given below being intended to express any restriction thereto:

I. Synthetic organic high-molecular materials:

a. Polymerisation products based on organic compounds containing at least one polymerisable carbon-carbon double bond, that is to say their homopolymers or copolymers as well as their after-treatment products such as, for example, crosslinking, grafting or degradation products, polymer blends or products obtained by modification of reactive groups, for example polymers based on α,β-unsaturated carboxylic acids or derivatives of such carboxylic acids, especially on acrylic compounds (such as, for example, acrylic esters, acrylic acid, acrylonitrile, acrylamides and their derivatives or their methacrylic analogues), on olefine hydrocarbons (such as, for example, ethylene, propylene, styrenes or dienes and also so-called ABS polymers), and polymers based on vinyl and vinylidene compounds (such as, for example, vinyl chloride, vinyl alcohol and vinylidene chloride), b. Polymerisation products such as are obtainable by ring opening, for example, polyamides of the polycaprolactam type, and also polymers which are obtainable both via polyaddition and via polycondensation, such as polyethers or polyacetals, c. Polycondensation products or precondensates based on bifunctional or polyfunctional compounds possessing condensable groups, their homocondensation and co-condensation products, and after-treatment products, such as, for example, polyesters, especially polyesters which are saturated (for example ethylene glycol terephthalic acid polyester) or unsaturated (for example maleic acid-dialcohol polycondensates as well as their crosslinking products with copolymerisable vinyl monomers), unbranched or branched (also including those based on polyhydric alcohols, such as, for example alkyd resins), polyamides (for example hexamethylenediamine adipate), maleate resins, melamine resins, their precondensates and analogues, polycarbonates and silicones, and d. Polyaddition products such as polyurethanes (crosslinked and non-crosslinked) and epoxide resins.

II. Semi-synthetic organic materials, for example, cellulose esters of varying degrees of esterification (so-called 2½-acetate or triacetate) or cellulose ethers, regenerated cellulose (viscose or cuprammonium cellulose), or their aftertreatment products, and casein plastics.

III. Natural organic materials of animal or vegetable origin, for example based on cellulose or proteins, such as cotton, wool, linen, silk, natural lacquer resins, starch and casein.

The organic materials to be optically brightened can be in the most diverse states of processing (raw materials, semi-finished goods or finished goods). On the other hand, they can be in the form of structures of the most diverse shapes, that is say, for example, predominantly threedimensional bodies such as slabs, profiles, injection mouldings, various machined articles, chips, granules or foams, and also as predominantly two-dimensional bodies such as films, sheets, lacquers, coverings, impregnations and coatings, or as predominantly one-dimensional bodies such as filaments, fibres, flocks and wires. The said materials can, on the other hand, also be in an unshaped state, in the most diverse homogeneous or inhomogeneous forms of division, such as, for example, in the form of powders, solutions, emulsions, dispersions, latices, pastes or waxes.

Fibre materials can, for example, be in the form of continuous filaments (stretched or unstretched), staple fibres, flocks, hanks, textile filaments, yarns, threads, fibre fleeces, felts, waddings, flocked structures or woven textile fabrics, textile laminates, knitted fabrics and papers, cardboards or paper pulps.

The compounds to be used according to the invention are of importance, inter alia, for the treatment of organic textile materials, expecially woven textile fabrics. Where fibres, which can be in the form of staple fibres or continuous filaments or in the form of hanks, woven fabrics, knitted fabrics, fleeces, flocked substrates or laminates, are to be optically brightened according to the invention, this is advantageously effected in an aqueous medium, wherein the compounds in question are present in a finely divided form (suspensions, so-called microdispersions or possibly solutions). If desired, dispersing agents, stabilisers, wetting agents and further auxiliaries can be added during the treatment.

Depending on the type of brightener compound used, it may prove advantageous to carry out the treatment in a neutral or alkaline or acid bath. The treatment is usually carried out at temperatures of about 20° to 140° C, for example at the boiling point of the bath or near it (about 90° C). Solutions or emulsions in organic solvents can also be used for the finishing, according to the invention, of textile substrates, as is practised in the dyeing trade in so-called solvent dyeing (pad-thermofix application, or exhaustion dyeing process in dyeing machines).

The new optical brighteners according to the present invention can further be added to, or incorporated in, the materials before or during their shaping. Thus they can, for example, be added to the compression moulding composition or injection moulding composition during the manufacture of films, sheets (for example, hot milling into polyvinyl chloride) or mouldings.

Where fully synthetic or semi-synthetic organic materials are being shaped by spinning processes or via spinning compositions, the optical brighteners can be applied in accordance with the following processes:

Addition to the starting substances (for example monomers) or intermediates (for example precondensates or prepolymers), that is to say before or during the polymerisation, polycondensation or polyaddition, powdering onto polymer chips or granules for spinning compositions, bath dyeing of polymer chips or granules for spinning compositions, metered addition to spinning melts or spinning solutions, and application to the tow before stretching.

The new optical brighteners according to the present invention can, for example, also be employed in the following use forms:

a. Mixed with dyestuffs (shading) or pigments (coloured pigments or especially, for example, white pigments), or as an additive to dye baths, printing pastes, discharge pastes or reserve pastes, or for the aftertreatment of dyeings, prints or discharge prints.

b. Mixed with so-called "carriers", wetting agents, plasticisers, swelling agents, anti-oxidants, light stabilisers, heat stabilisers and chemical bleaching agents (chlorite bleach or bleaching bath additives).

c. Mixed with crosslinking agents or finishing agents (for example starch or synthetic finishes), and in combination with the most diverse textile finishing processes, especially synthetic resin finishes (for example creaseproof finishes such as "wash-and-wear", "permanent-press" or "no-iron"), as well as flameproof finishes, soft handle finishes, anti-soiling finishes or anti-static finishes, or anti-microbial finishes.

d. Incorporation of the optical brighteners into polymeric carriers (polymerisation, polycondensation or polyaddition products), in a dissolved or dispersed form, for use, for example, in coating agents, impregnating agents or binders (solutions, dispersions and emulsions) for textiles, fleeces, paper and leather.

e. As additives to so-called "master batches".

f. As additives to the most diverse industrial products in order to render these more marketable (for example to improve the appearance of soaps, detergents and pigments).

g. In combination with other optically brightening substances, h. In spinning bath preparations, that is to say as additives to spinning baths such as are used for improving the slip for the further processing of synthetic fibres, or from a special bath before stretching the fibre.

i. As scintillators for various purposes of a photographic nature, such as, for example, for electrophotographic reproduction or supersensitisation, and for the optical brightening of photographic layers, optionally in combination with white pigments such as, for example, $TiO_2$.

If the brightening process is combined with textile treatment methods or finishing methods, the combined treatment can in many cases advantageously be carried out with the aid of appropriate stable preparations which contain the optically brightening compounds in such concentration that the desired brightening effect is achieved.

In certain cases, the brighteners are made fully effective by an after-treatment. This can, for example, represent a chemical treatment (for example acid treatment), a thermal treatment (for example heat) or a combined chemical/thermal treatment. Thus, for example, the appropriate procedure to follow in optically brightening a range of fibre substrates, for example polyester fibres, with the brighteners according to the invention, is to impregnate these fibres with the aqueous dispersions (optionally also solutions) of the brighteners at temperatures below 75° C, for example at room temperature, and to subject them to a dry heat treatment at temperatures above 100° C, it being generally advisable additionally to dry the fibre material beforehand at a moderately elevated temperature, for example at not less than 60° C and up to about 130° C. The heat treatment in the dry state is then advantageously carried out at temperatures between 120° and 225° C, for example by warming in a drying chamber, by ironing within the specified temperature range or by treatment with dry, superheated steam. The drying and dry heat treatment can also be carried out in immediate succession or be combined in a single process stage.

The amount of the new optical brighteners to be used according to the invention, relative to the material to be optically brightened, can vary within wide limits. A distinct and durable effect is achievable even with very small amounts, in certain cases, for example, amounts of 0.0001 percent by weight. However, amounts of up to about 0.8 percent by weight and optionally of up to about 2 percent by weight can be employed. For most practical purposes, amounts between 0.0005 and 0.5 percent by weight are of preferred interest.

The new optical brighteners are also particularly suitable for use as additives for wash liquors or industrial and domestic washing agents, to which they can be added in various ways. They are appropriately added to wash liquors in the form of their solutions in water or organic solvents or in a finely divided form, as aqueous dispersions. They are advantageously added to domestic or industrial washing agents in any stage of the manufacturing process of the washing agents, for example to the so-called "slurry" before spray-drying to the washing powder, or during the preparation of liquid washing agent combinations. They can be added either in the form of a solution or dispersion in water or other solvents or, without auxiliaries, as a dry brightening powder. For example, the brighteners can be mixed, kneaded or ground with the detergent substances and, in this form, admixed to the finished washing powder. However, they can also be sprayed in a dissolved or pre-dispersed form onto the finished washing agent.

Possible washing agents are the known mixtures of detergent substances such as, for example, soap in the form of chips and powders, synthetics, soluble salts of sulphuric acid half esters of higher fatty alcohols, arylsulphonic acids with higher and/or multiple alkyl substituents, sulphocarboxylic acid esters of medium to higher alcohols, fatty acid acylaminoalkyl- or acylaminoaryl-glycerolsulphonates, phosphoric acid esters of fatty alcohols and the like. Possible so-called "builders" which can be used are, for example, alkali metal polyphosphates and polymetaphosphates, alkali metal pyrophosphates, alkali metal salts of carboxymethylcellulose and other "soil redeposition inhibitors", and also alkali metal silicates, alkali metal carbonates, alkali metal borates, alkali metal perborates, nitrilotriacetic acid, ethylenediaminotetraacetic acid, and foam stabilisers, such as alkanolamides of higher fatty acids. The washing agents can further contain, for example: antistatic agents, skin protection agents which restore fat, such as lanolin, enzymes, antimicrobial agents, perfumes and dyestuffs.

The new optical brighteners have the particular advantage that they are also active in the presence of active chlorine donors, such as, for example, hypochlorite, and can be used without significant loss of the effects in wash liquors containing non-ionic washing agents, for example alkylphenol polyglycol ethers.

The compounds according to the invention are added in amounts of 0.0005–1% or more, relative to the weight of the liquid or pulverulent, finished washing agent. Wash liquors which contain the indicated amounts of the optical brighteners claimed impart a brilliant appearance in daylight when used to wash textiles of cellulose fibres, polyamide fibres, cellulose fibres with a high quality finish, polyester fibres, wool and the like.

The washing treatment is carried out, for example, as follows:

The textiles quoted are treated for 1 to 30 minutes at 20° to 100° C in a wash liquor which contains 1 to 10 g/kg of a composite washing agent containing a builder and 0.05 to 1%, relative to the weight of washing agent, of the brighteners claimed. The liquor ratio can be 1:3 to 1:50. After washing, rinsing and drying are carried out as usual. The wash liquor can contain 0.2 g/l of active chlorine (for example as hypochlorite) or 0.1 to 2 g/l of sodium perborate, as a bleaching additive.

The compounds according to the invention can, depending on their substituents, be used as laser dyestuffs.

In the examples, unless otherwise specified, percentages are always percentages by weight. Unless otherwise noted, melting points and boiling points are uncorrected.

EXAMPLE 1

10.1 g of potassium t-butylate are introduced into a solution of 7.1 g of 5,6-dimethyl-2-(p-tolyl)-benzoxazole and 9.3 g. of the sodium salt of p-benzaldehyde-sulphonic acid anil in 360 ml of anhydrous dimethylformamide, at 50° C and while stirring vigorously and passing nitrogen over the mixture, a violet coloration being formed. The temperature is kept at 60° C for 1 hour, first by slight cooling and then by warming. After cooling in an ice bath, 720 ml of water are added and the mixture is neutralised with about 9 ml of concentrated hydrochloric acid. The precipitated product is filtered off, washed with three times 50 ml of water and dried in vacuo. This gives 11.0 g of the crude sulphonic acid of the formula

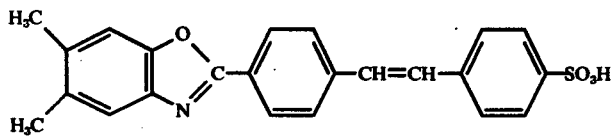
(101)

as the potassium salt, mixed with some sodium salt. It is purified by being extracted by boiling with 150 ml of chloroform and then with 40 ml of dimethylformamide and is recrystallised from a 3:2 mixture of dimethylformamide-water with the aid of active charcoal for decolorisation.

The potassium (Na) salt of the compound of the formula

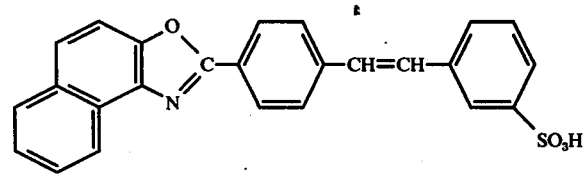
(102)

is obtained in a similar manner from 2-(p-tolyl)-naphth(1,2-d)oxazole and the sodium salt of m-benzaldehydesulphonic acid anil.

EXAMPLE 2

18.4 g of the potassium salt of biphenyl-4-aldehyde-4'-sulphonic acid, 89.2% strength, in 50 ml of aniline and 50 ml of dimethylformamide are stirred under reflux for ½ hour. The suspension is evaporated completely in vacuo at 130° C. 10.45 g of 2-(p-tolyl)-benzoxazole and 100 ml of anhydrous dimethylformamide are added to the residue (anil) and 16.8 g of potassium t-butylate are introduced into the resulting suspension at 50° C, while stirring and passing nitrogen over the mixture. The temperature is allowed to rise to 60° C and the mixture is kept at 60° C for 1 hour, cooled in an ice bath, treated with 300 ml of deionised water and neutralised with 14 ml of concentrated hydrochloric acid. The product is filtered off, washed repeatedly with water and dried. This gives 27.0 g of the crude potassium salt of the sulphonic acid of the formula

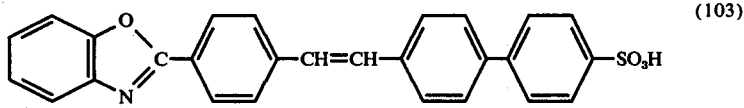
(103)

This is purified by being recrystallised from 800 ml of dimethylsulphoxide, extracted with boiling chloroform, alcohol and water and dried.

Yield: 13.0 g of pale yellow powder.

EXAMPLE 3

The potassium/sodium salts of the compounds of the general formula (104), listed in Table I, can be obtained in a manner similar to that described in Example 1 or 2.

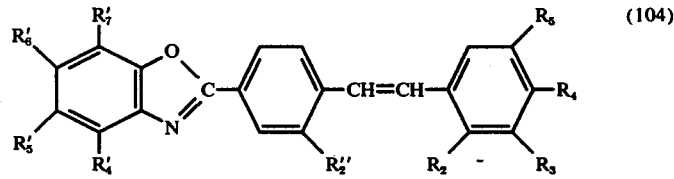
(104)

TABLE I

Empty spaces denote hydrogen

| Formula No. | R'4 | R'5 | R'6 | R'7 | R''2 | R2 | R3 | R4 | R5 |
|---|---|---|---|---|---|---|---|---|---|
| (105) |  | CH₃ | CH₃ |  |  | SO₃H |  |  |  |
| (106) |  | CH₃ | CH₃ |  |  |  | SO₃H |  |  |
| (107) |  | CH₃ | CH₃ |  | SO₃H |  |  | —C(CH₃)₃ |  |
| (108) |  |  | OCH₃ |  |  | SO₃H |  | Cl |  |
| (109) |  |  | OCH₃ |  |  |  | SO₃H |  |  |
| (110) |  |  | OCH₃ |  |  |  |  | SO₃H |  |
| (111) |  |  | OCH₃ |  | SO₃H |  |  |  |  |
| (112) | OCH₃ |  |  |  |  | Cl |  |  | SO₃H |
| (113) | OCH₃ |  |  |  |  |  | SO₃H |  |  |
| (114) | OCH₃ |  |  |  |  |  |  | SO₃H |  |
| (115) | OCH₃ |  |  |  | SO₃H |  |  |  |  |
| (116) | OCH₃ | OCH₃ |  |  |  | SO₃H |  |  |  |
| (117) | OCH₃ | OCH₃ |  |  |  |  | SO₃H |  |  |

TABLE I-continued

Empty spaces denote hydrogen

| Formula No. | R'$_4$ | R'$_5$ | R'$_6$ | R'$_7$ | R''$_2$ | R$_2$ | R$_3$ | R$_4$ | R$_5$ |
|---|---|---|---|---|---|---|---|---|---|
| (118) | | OCH$_3$ | OCH$_3$ | | | | | SO$_3$H | |
| (119) | | OCH$_3$ | OCH$_3$ | | SO$_3$H | | | | |
| (120) | —CH=CH—CH=CH— | | | | SO$_3$H | | | | |
| (121) | | —CH$_2$—CH$_2$—CH$_2$— | | | | SO$_3$H | | | |
| (122) | | —CH$_2$—CH$_2$—CH$_2$— | | | | | SO$_3$H | | |
| (123) | SO$_3$H | | | | | OCH$_3$ | | | |
| (124) | | | | | SO$_3$H | OCH$_3$ | | | |
| (125) | SO$_3$H | | | | | | | C$_6$H$_5$ | |
| (126) | | SO$_3$H | | | | | | C$_6$H$_5$ | |
| (127) | SO$_3$H | | | Cl | | | | C$_6$H$_5$ | |
| (128) | SO$_3$H | | | | | | —CH=CH—CH=CH— | | |
| (129) | | | | | SO$_3$H | | | C$_6$H$_5$ | |
| (130) | SO$_3$H | | | | | OCH$_3$ | | | |
| (131) | CH$_3$ | | | CH$_3$ | SO$_3$H | OCH$_3$ | | | |
| (132) | | —C(CH$_3$)$_3$ | | | | OCH$_3$ | | OCH$_3$ | SO$_3$H |
| (133) | CH$_3$ | | | CH$_3$ | | OCH$_3$ | | | SO$_3$H |
| (134) | CH$_3$ | | | CH$_3$ | | | | p-C$_6$H$_4$—SO$_3$H | |
| (135) | | —C(CH$_3$)$_3$ | | | | | | p-C$_6$H$_4$—SO$_3$H | |
| (136) | CH$_3$ | | | | | | | p-C$_6$H$_4$—SO$_3$H | |
| (137) | | —C(CH$_3$)(C$_6$H$_5$)CH$_3$ | | | | | | p-C$_6$H$_4$—SO$_3$H | |
| (138) | —C$_6$H$_{11}$ | | | | | | | p-C$_6$H$_4$—SO$_3$H | |
| (139) | | —SO$_2$NHCH$_3$ | | | | | | p-C$_6$H$_4$—SO$_3$H | |
| (140) | Cl | | | | | | | p-C$_6$H$_4$—SO$_3$H | |
| (141) | | | | CH$_3$ | | | | p-C$_6$H$_4$—SO$_3$H | |
| (142) | —CH(CH$_3$)$_2$ | | | | | | | p-C$_6$H$_4$—SO$_3$H | |
| (143) | sec.—C$_4$H$_9$ | | | | | | | p-C$_6$H$_4$—SO$_3$H | |
| (144) | —C(CH$_3$)$_3$ | | | CH$_3$ | | | | p-C$_6$H$_4$—SO$_3$H | |
| (145) | | | | | SO$_3$H | | | C$_6$H$_5$ | |
| (146) | | —C(CH$_3$)$_3$ | | | SO$_3$H | OCH$_3$ | | | |

The dimethylamine salts which are sometimes formed in part, can be converted into the potassium salts by heating with aqueous potassium carbonate solution, the dimethylamine liberated being removed by distillation with water.

The chlorine-containing compounds of the formulae (108) and (112) are prepared at room temperature, in distinction from the other products.

EXAMPLE 4

11.1 g of the potassium salt of biphenyl-4-aldehyde-4'-sulphonic acid, 89.2% strength, in 50 ml of aniline and 50 ml of dimethylformamide are stirred under reflux for ½ hour. The suspension is evaporated completely in vacuo at 130° C. 10.0 g of the compound of the formula

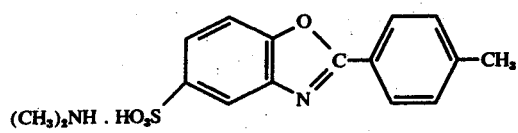

(British Pat. No. 1,141,956) and 100 ml of anhydrous dimethylformamide are added to the residue and 10.1 g of potassium t-butylate are introduced into the resulting suspension at 50° C, while stirring and passing nitrogen over the mixture. The temperature is kept at 60° C for 1 hour, first by cooling and then by warming, and the mixture is cooled in an ice bath, treated with 200 ml of deionised water and neutralised with about 9 ml of concentrated hydrochloric acid. After filtering off the product, washing it repeatedly with deionised water and drying it in vacuo, 13.3 g of a beige product are obtained.

This product is stirred in 100 ml of phosphorus oxychloride for 1 hour under reflux and the mixture is cooled. It is filtered and the residue is washed repeatedly with acetone, ice water and acetone again and is dried in vacuo, first at 40° C and then at 80° C. After recrystallisation from anhydrous o-dichlorobenzene, 8.7 g of the disulphonic acid chloride of the formula

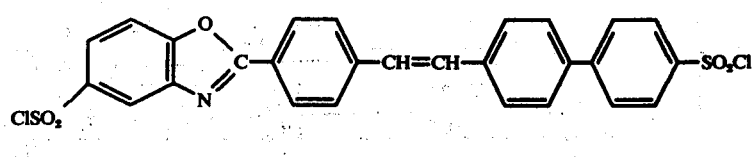

(147)

are obtained as light yellow crystals of melting point 315° C (decomposition).

8.2 g of this compound in 50 ml of pyridine and 2ml of distilled water are heated under reflux for ½ hour. 10 ml of the water-pyridine mixture are distilled off and the mixture is cooled and filtered and the product is washed repeatedly with alcohol. After drying, 8.6 g of the compound of the formula

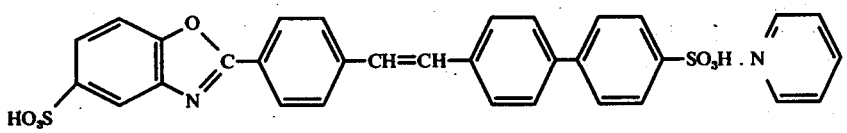
(148)

are obtained.

According to the above described process particularly these compounds of formula (1) are prepared wherein $R_1$ and/or $R_5$ are sulpho.

EXAMPLE 5

The crude potassium salt of the compound of the formula (129), listed in Table I, is converted into the sulphochloride by boiling up with phosphorus oxychloride and this sulphochloride is stirred with aqueous dimethylformamide. This gives the compound of the formula

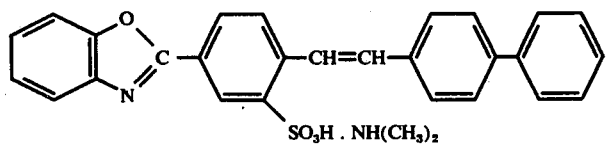
(149)

which is recrystallised from n-propanol-water.

In a corresponding manner, the potassium salt of the formula (103) gives the sulphochloride of melting point 280° C (decomposition) (from o-dichlorobenzene) and the latter gives the compound of the formula

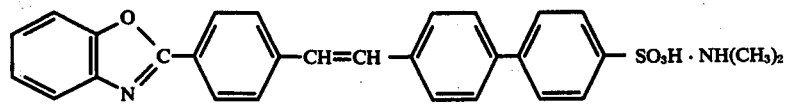
(150)

In a corresponding manner, the potassium salt of the formula (134) gives the sulphochloride of melting point 247° C (from chlorobenzene) and the latter gives, by saponification with aqueous pyridine (see Example 4), the compound of the formula

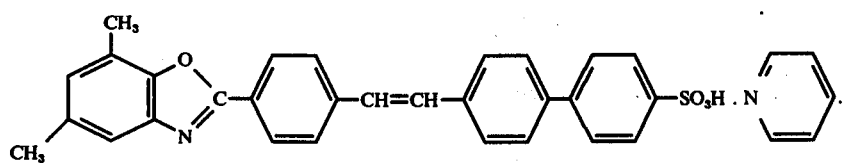
(151)

EXAMPLE 6

3.8 g of sodium methylate (91.4% strength) are introduced over the course of 10 minutes into a solution of 17.3 g of the compound of the formula

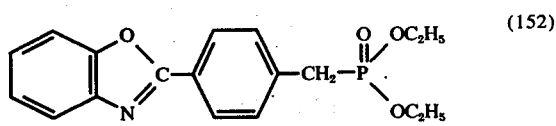
(152)

and 16.9 g of the sodium salt of 2,3-dimethoxybenzaldehyde-5-sulphonic acid (87.4% strength) in 100 ml of anhydrous dimethylformamide at 40°–45° C, while stirring well and passing nitrogen over the mixture. After the sodium methylate has been introduced, the mixture is stirred at 40 –45° C for a further 4 hours. After cooling to 5° C the product which has crystallised out is filtered off and dried in vacuo. After recrystallisation from 200 ml of a mixture of 160 ml of alcohol and 40 ml of water, 5.7 g of the compound of the formula

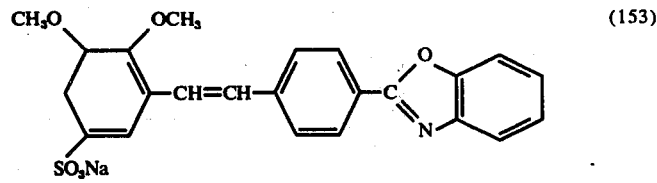
(153)

are obtained as a pale yellow crystalline powder.

2,3-Dimethoxybenzaldehyde-5-sulphonic acid can be obtained as follows: 49.9 g of 2,3-dimethoxybenzaldehyde are introduced at 5°—10° C into 170 g of 5% strength oleum. After this, the brown solution is stirred at room temperature for 24 hours. A further 65 g of 25% strength oleum are then added, cooling by means of ice water being used to ensure that the temperature does not exceed 35° C. The mixture is stirred at room temperature for an additional 2 hours and poured out onto 500 g of ice, the brown solution is neutralised with approx. 1.7 kg of barium carbonate and warmed to 80° C and the precipitated barium sulphate is filtered off and rinsed with 500 ml of hot water. The clear filtrate is warmed to 80° C and 176 ml of solution of 15.9 g of sodium carbonate in 200 ml of water are added, and the mixture is clarified by filtration and the clear filtrate is evaporated to dryness and the residue is dried in vacuo. This gives 62.5 g of the sodium salt of 2,3 dimethoxybenzaldehyde-5-sulphonic acid of 87.4% strength.

EXAMPLE 7

11.9 g of the compound of the formula

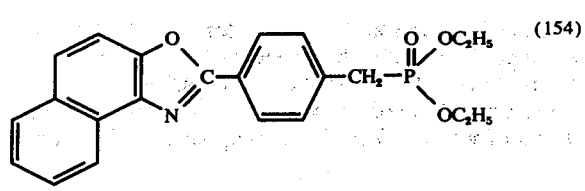 (154)

and 11.1 g of the disodium salt of benzaldehyde-2,4-disulphonic acid (92.7% strength) are condensed, as described in Example 6, in 100 ml of anhydrous dimethylsulphoxide by adding 2.3 g of sodium methylate (91.0% strength). After the reaction is completed the reaction mixture is poured into 1,000 ml of water, heated to the boil and clarified by filtration and 200 g of sodium chloride are added. The product which crystallises out is filtered off after cooling, washed with a solution of 300 g of sodium chloride in 1 liter of water and dried in vacuo. After recrystallising twice from a mixture of 240 parts by volume of ethanol and 60 parts by volume of water, 6.5 g of the compound of the formula

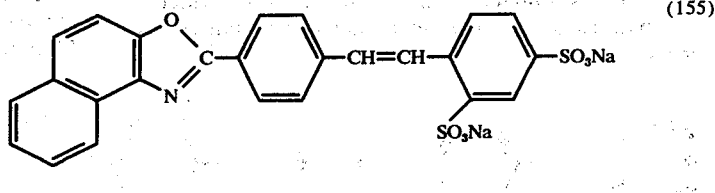 (155)

are obtained as a yellow crystalline powder.

The phosphonate of the formula (154), of melting point 82°–83° C, can be obtained by known methods from 2-(p-tolyl)-naphth(1,2-d) oxazole by brominating with N-bromosuccinimide in boiling carbon tetrachloride and adding dibenzoyl peroxide and reacting the monobromo compound with triethyl phosphite at 140°–45° C.

The compounds of the general formula (156), listed in Table II, can be obtained in a similar manner.

TABLE II

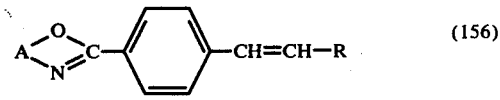 (156)

| No | A | $R_1$ | R |
|---|---|---|---|
| (157) | naphthyl | H | 3,5-disulfonatophenyl (NaO$_3$S / SO$_3$Na) |
| (158) | naphthyl | H | 3-chloro-4-sulfonatophenyl (Cl / SO$_3$Na) |
| (159) | naphthyl | H | 3-methyl-4-sulfonatophenyl (CH$_3$ / SO$_3$Na) |

TABLE II-continued structure (156): A-oxadiazole-C₆H₄-CH=CH-R

| No | A | R₁ | R |
|---|---|---|---|
| (160) | naphthalene-1,2-diyl | H | 2-(SO₃Na)-phenyl |
| (161) | 4-CH₃O-phenyl (1,2-disubst.) | H | 2-(SO₃Na)-phenyl |
| (162) | phenyl | H | 3,4-di(SO₃Na)-phenyl |
| (163) | phenyl | H | 3-OCH₃-4-(SO₃Na)-phenyl |
| (164) | phenyl | H | 3-CH₃O-4-(SO₃Na)-phenyl |
| (165) | phenyl | H | 3-(NaO₃S)-4-CN-phenyl |
| (166) | phenyl | H | 3-(NaO₃S)-4-COOCH₃-phenyl |
| (167) | 4-CH₃O-phenyl | H | 2-(NaO₃S)-phenyl |
| (168) | 4-(CH₃OOC)-phenyl | H | 4′-(SO₃Na)-biphenyl-4-yl |
| (169) | 4-(C₂H₅-SO₂)-phenyl | H | 4′-(SO₃Na)-biphenyl-4-yl |

TABLE II-continued

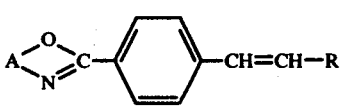

| No | A | R₁ | R |
|---|---|---|---|
| (170) | 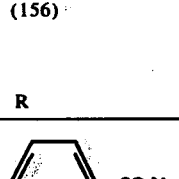 | H | 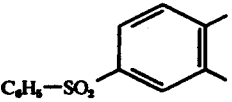 |
| (171) | 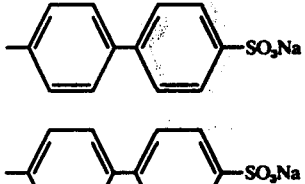 | H | 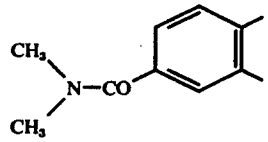 |
| (172) | 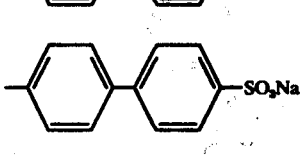 | H | 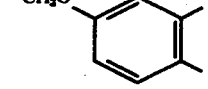 |
| (173) | 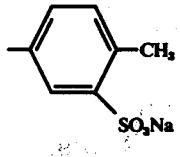 | H | 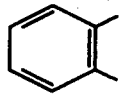 |
| (174) | 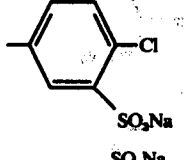 | Cl | 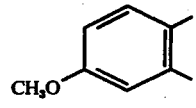 |
| (175) | 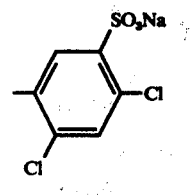 | H | 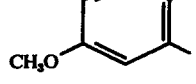 |
| (176) | 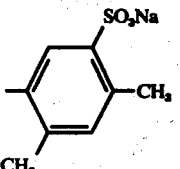 | H | 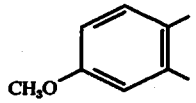 |
| (177) | 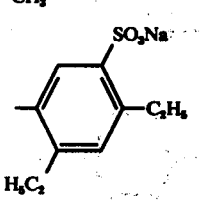 | H | |

Saponification of the compound No. (168), for example with sodium hydroxide solution, gives the Na salt of the corresponding carboxylic acid, and acidifying the latter with hydrochloric acid gives the corresponding carboxylic acid.

EXAMPLE 8

A polyamide fibre fabric (Perlon-Helanca) is washed for 15 minutes, using a liquor ratio of 1:20, in a liquor warmed to 50° C which contains the following additives per liter:

0.004 to 0.016 g of a brightener of the formulae (102), (125), (134), (149), (151), (153), (159), (160), (163), (164) or (167), 0.25 g of active chlorine (Javelle water) and 4 g of a washing powder of the following composition:

15.00% of dodecylbenzenesulphonate,
10.00% of sodium laurylsulphonate, 40.00% of sodium tripolyphosphate,
25.75% of anhydrous sodium sulphate,
7.00% of sodium metasilicate,
2.00% of carboxymethylcellulose and
0.25% of ethylenediaminetetraacetic acid.

The polyamide fibre fabric is not introduced into the wash liquor, warmed to 50° C, until 15 minutes after the latter has been prepared. After rinsing and drying, the fabric exhibits a good brightening effect.

The washing powder of the composition given above can also contain the brighteners of the formulae designated above, directly incorporated.

EXAMPLE 9

Bleached cotton material is washed for 15 minutes, using a liquor ratio of 1 : 20, in a liquor warmed to 50° C which contains the following additives per liter:
 0.004 g of a brightener of the formulae (102), (125), (134), (136), (148), (151), (157), (159), (160) or (164),
 0.25 g of active chlorine (Javelle water) and
 4 g of a washing powder of the following composition:
   15.00% of dodecylbenzenesulphonate,
   10.00% of sodium laurylsulphonate,
   40.00% of sodium tripolyphosphate,
   25.75% of anhydrous sodium sulphate,
   7.00% of sodium metasilicate,
   2.00% of carboxymethylcellulose and
   0.25% of ethylenediaminetetraacetic acid.

The cotton material is not introduced into the bath until 15 minutes after the preparation of the wash liquor, warmed to 50° C. After rinsing and drying, the fabric exhibits a good brightening effect with good fastness to chlorine.

The washing powder of the composition indicated above can also contain the brighteners of the formulae designated above, directly incorporated.

EXAMPLE 10

A polyamide fibre fabric (Perlon) is introduced, at a liquor ratio of 1:40 and at 60° C, into a bath which contains (relative to the weight of the material) 0.05% of a brightener of the formulae (101), (102), (103), (125), (126), (134), (135), (136), (148), (149), (150), (151), (153), (155), (157), (159), (160), (161), (162), (163), (164) or (167) and, per liter, 1 g of 80% strength acetic acid and 0.25 g of a product of the addition reaction of 30 to 35 mols of ethylene oxide with one mol of technical grade stearyl alcohol. The bath is warmed to the boil over the course of 30 minutes and is kept at the boil for 30 minutes. After rinsing and drying, a good brightening effect is obtained.

Similar brightening effects are obtained if, instead of the fabric of polyamide 6, a fabric of polyamide 66 (nylon) is used.

Finally, it is also possible to work under high temperature conditions, for example for 30 minutes at 130° C. The addition of 3 g/l of hydrosulphite is advisable for this method of application.

EXAMPLE 11

10,000 g of a polyamide prepared in a known manner from hexamethylenediamine adipate are mixed for 12 hours, in the form of chips, in a tumbler with 30 g of titanium dioxide (rutile modification) and 5 g of one of the compounds of the formulae (101), (102), (103), (125), (126), (135), (148), (149), (151), (153), (155), (157), (159) to (164) or (167). The chips treating in this way are melted, after displacing the atmospheric oxygen by steam, in a kettle heated to 300 to 310° C by means of oil or diphenyl vapour, and the mixture is stirred for half an hour. The melt is then extruded through a spinneret under a nitrogen pressure of 5 atmospheres gauge and the filament spun in this manner is cooled and wound up on a spinning bobbin. The resulting filaments exhibit a good brightening effect.

Similarly good results are obtained if, instead of a polyamide prepared from hexamethylenediamine adipate, a polyamide prepared from ε-caprolactam is used.

EXAMPLE 12

Bleached cotton material is washed for 30 minutes at 95° C, using a liquor ratio of 1:20. The wash liquor contains the following additives per liter:
 0.004 g of a brightener of the formulae (102), (125), (134), (136), (148), (151), (159), (160) or (164) and
 4 g of a washing powder of the following composition:
   40.0% of soap flakes,
   15.0% of sodium tripolyphosphate,
   8.0% of sodium perborate,
   1.0% of magnesium silicate,
   11.0% of sodium metasilicate (9 $H_2O$),
   24.6% of calcined sodium carbonate and
   0.4% of ethylenediaminetetraacetic acid.

After rinsing and drying, the cotton fabric exhibits a good brightening effect.

EXAMPLE 13

An article of cotton material which has been given a non-iron finish by means of aminoplast resin is washed, at a liquor ratio of 1:20, for 15 minutes in a liquor, warmed to 55° C, which contains the following additives per liter:
 0.004 to 0.016 g of a brightener of the formulae (102), (134), (148), (151), (159) or (160) and
 4 g of a washing powder of the following composition:
   15.00% of dodecylbenzenesulphonate,
   10.00% of sodium laurylsulphonate,
   40.00% of sodium tripolyphosphate,
   25.75% of anhydrous sodium sulphate,
   7.00% of sodium metasilicate,
   2.00% of carboxymethylcellulose and
   0.25% of ethylenediaminetetraacetic acid.

After rinsing and drying, the fabric exhibits a strong brightening effect with good fastness to light.

EXAMPLE 14

An aqueous suspension of 100 parts of cellulose in 4,000 parts of water is mixed with an aqueous solution of 0.1 part of the brightener of the formula (148) for 15 minutes in a hollander, two parts of resin suspension and 3 parts of aluminium sulphate are added and the mixture is diluted with 20,000 parts of return water containing 1 g of aluminium sulphate per liter, and converted in the customary manner into paper sheets. The resulting paper sheets are strongly brightened.

EXAMPLE 15

2 g of the optical brightener of the formula (148) are dissolved in about 50 ml of hot, distilled water. 80 g of a degraded starch are separately dissolved to form a colloidal solution in 1,000 ml of water heated to 90° C. The brightener solution is then incorporated into the starch solution. The resulting solution can have a pH value of 8 to 9.

A sized printing paper is coated on its surface with this sizing liquor in a sizing press, and the coated paper is dried at about 90°–120° C in the drying section of the paper machine.

This gives a paper with a significantly improved degree of whiteness.

Similarly good results are obtained using a pigment coating liquor of a synthetic resin dispersion which contains aluminium magnesium silicate.

EXAMPLE 16

A casting composition consisting of 10 g of polyacrylonitrile, 0.2 g of titanium dioxide (anatase modification) as delustring agent and 40 ml of dimethylformamide and containing 5 mg of one of the compounds of the formulae (125), (126), (149), (151), (155) or (157), is cast on a glass plate and drawn out into a thin film by means of a metal rod.

After drying, the film is strongly brightened.
What we claim is:
1. A stilbene compound of the formula

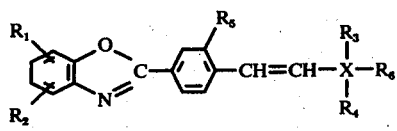

wherein
X denotes a 4-biphenyl radical, $R_1$ denotes hydrogen, alkyl having 1 to 4 carbon atoms, chlorine, cyclohexyl, carbalkoxy having 2 to 5 carbon atoms, carboxyl or sulpho,
$R_2$ denotes hydrogen or alkyl having 1 to 4 carbon atoms,
$R_3$ denotes hydrogen or sulpho,
$R_4$ denotes hydrogen,
$R_5$ denotes hydrogen, or sulpho, and
$R_6$ denotes hydrogen or sulpho, the molecule containing at least one but not more than two sulpho groups.

2. A stilbene compound according to claim 1, of the formula

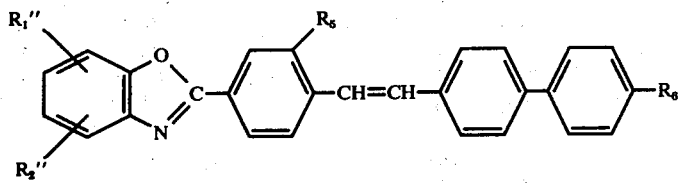

wherein $R_1''$ denotes hydrogen, alkyl having 1 to 4 carbon atoms, chlorine, cyclohexyl, carbalkoxy having 2 to 5 carbon atoms, carboxyl, $R_2''$ denotes hydrogen or alkyl having 1 to 4 carbon atoms, $R_5$ denotes hydrogen, or sulpho and $R_6$ denotes hydrogen or sulpho, and the molecule contains at least one but not more than two sulpho groups.

3. A stilbene compound according to claim 2, of the formula

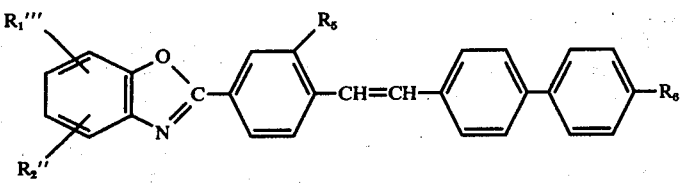

wherein $R_1'''$ denotes hydrogen, alkyl having 1 to 4 carbon atoms, chlorine, cyclohexyl, carboxyl or sulpho and $R_2''$ denotes hydrogen or alkyl having 1 to 4 carbon atoms, and $R_5$ and $R_6$ have the meaning indicated in claim 2 and the molecule contains at least one but not more than two sulpho groups.

4. A stilbene compound according to claim 3, of the formula

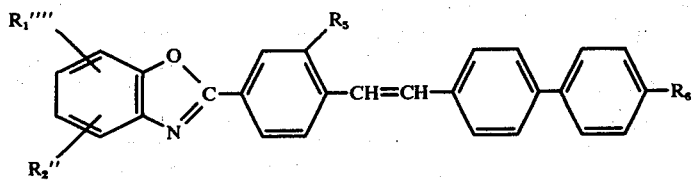

wherein $R_1''''$ denotes hydrogen, alkyl having 1 to 4 carbon atoms, chlorine, cyclohexyl, sulpho or carbalkoxy having 2 to 5 carbon atoms, and $R_2''$ denotes hydrogen or alkyl having 1 to 4 carbon atoms, and $R_5$ and $R_6$ have the meaning indicated in claim 3.

5. A stilbene compound according to claim 4, of the formula

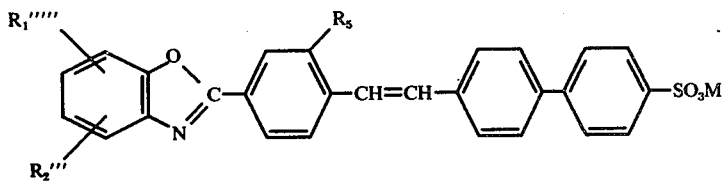

wherein $R_1''''''$ denotes hydrogen, alkyl having 1 to 4 carbon atoms, chlorine or carbalkoxy having 2 to 5 carbon atoms, $R_2'''$ denotes hydrogen, or methyl, and M denotes a hydrogen ion, alkali metal ion, alkaline earth metal ion, ammonium ion or amine salt ion, and $R_5$ has the meaning indicated in claim 4.

6. A compound of claim 1 having the formula

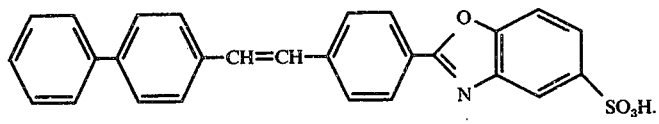

7. A compound of claim 1 having the formula

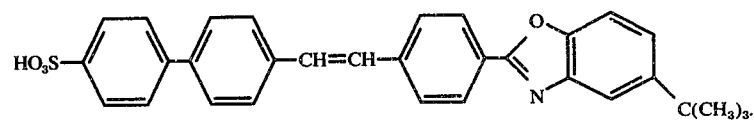

8. A compound of claim 1 having the formula

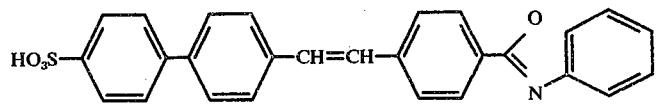

* * * * *

UNITED STATES PATENT AND TRADEMARK OFFICE
CERTIFICATE OF CORRECTION

PATENT NO. : 4,014,870
DATED : March 29, 1977
INVENTOR(S) : HANS RUDOLF MEYER

It is certified that error appears in the above—identified patent and that said Letters Patent are hereby corrected as shown below:

Col. 28, claim 3, line 45, after "cyclohexyl," insert

-- carbalkoxy having 2 to 5 carbon atoms --.

Signed and Sealed this

Seventh Day of June 1977

[SEAL]

Attest:

RUTH C. MASON
Attesting Officer

C. MARSHALL DANN
Commissioner of Patents and Trademarks